United States Patent [19]

Antonaroli et al.

[11] Patent Number: 5,010,204
[45] Date of Patent: Apr. 23, 1991

[54] ACETAZOLAMIDE-RELATED COMPOUNDS, PROCESS FOR THEIR PREPARATION, AND PHARMACEUTICAL COMPOSITION CONTAINING THE SAME

[75] Inventors: Simonetta Antonaroli; Bianco Armandodariano, both of Rome; Brufani Mario, Cestel Gundolfo; Lo Baido Giuseppe; Rende Giorgio, both of Rome, all of Italy

[73] Assignee: Instituto Chimico Internazionale Dr. Giuseppe Rende S.r.l., Rome, Italy

[21] Appl. No.: 381,453

[22] Filed: Jul. 18, 1989

[30] Foreign Application Priority Data

Jul. 29, 1988 [IT] Italy ................................ 48251 A/88

[51] Int. Cl.$^5$ ........................................... C07D 285/08
[52] U.S. Cl. ..................................................... 548/128
[58] Field of Search ............................... 548/139, 128

[56] References Cited

U.S. PATENT DOCUMENTS 4,151,167  4/1979  Kirkpatrick ........................ 548/139
4,483,864 11/1984  Barfknecht et al. ................ 424/270

OTHER PUBLICATIONS

Tinker et al, J. Pharmacology and Experimental Therapeutics, vol. 218, pp. 600–607, 1981.
Vaughan et al, J. Organic Chemistry, vol. 21, pp. 700–701, 1956.
Chemical Abstracts, vol. 98, No. 4, Mar. 28, 1983, p. 596, Abstract No. 107226D.
Article by P. G. DeBenedetti et al., "A Quantum Chemical QSAR Analysis of Carbonic Anhydrase Inhibito by Heterocyclic Sulfonamides, Sulfonamide Carbonic Anhydrase Inhibitors: Quantum Chemical QSAR".

Primary Examiner—Jose G. Dees
Assistant Examiner—Deborah D. Carr
Attorney, Agent, or Firm—Richard Bushnell

[57] ABSTRACT

Compounds related to acetazolamide and to its N-methyl derivatives, of the formulae:

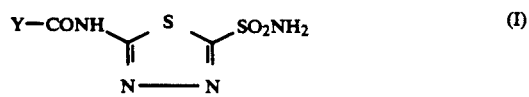

(I)

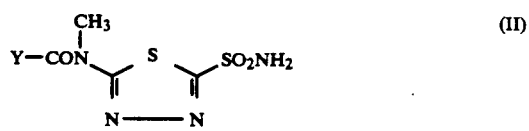

(II)

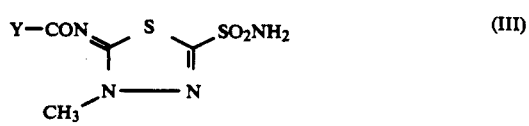

(III)

wherein Y is one of the following groups:

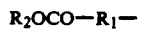

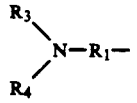

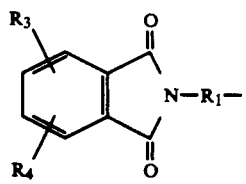

$R_1$ being a straight or branched alkylene or arylalkylene, or a phenylene, and the processes for their preparation; the compounds so obtained are inhibitors of carbonic anhydrase like acetazolamide but, in addition, they are well absorbed topically so that they can be used as drugs for treating glaucoma.

7 Claims, No Drawings

ACETAZOLAMIDE-RELATED COMPOUNDS, PROCESS FOR THEIR PREPARATION, AND PHARMACEUTICAL COMPOSITION CONTAINING THE SAME

This invention relates to novel acetazolamide-related compounds having inhibiting activity on carbonic anhydrase, which are useful in particular for treating glaucoma. More particularly, this invention relates to novel agents capable of inhibiting carbonic anhydrase, which are characterized in that they can be well absorbed locally, so that they are particularly suitable for topical administration.

The term glaucoma commonly means a variety of clinical conditions which are characterized by a progressive increase in intraocular pressure, a condition which gives rise to severe defects in the eye structures, up to optical atrophy. Various kinds of primary and secondary glaucoma are known, but all forms show a common feature, i.e. the increase of aqueous humour in the anterior chamber of the eye (camera anterior bulbi).

Various drugs are known that are capable of reducing the intraocular pressure, so that they could be employed for treating glaucoma, but their efficiency is variable and all of them show more or less serious side effects. Among such drugs, there are compounds showing cholinergic action (acetylcholine, pilocarpine and eserine), having a short-lasting action, compounds showing anticholinergic action, with remarkable side effects (atropine), compounds with adrenergic action (adrenalin), which are effective but painful, and compounds with antiadrenergic action (adrenergic beta-blocking agents).

These last compounds are the most commonly employed: thymolole, an adrenergic beta-blocking agent, is the most diffused product presently on the market in many countries; however, this class of drugs is also affected by undesired side effects, such as fits of asthma and cardiac troubles.

An additional class of compounds capable of reducing intra-ocular pressure, and therefore potentially useful for treating glaucoma, is the class of carbonic anhydrase inhibitors, the best known among them being acetazolamide. These compounds, though remarkably efficient, cannot be absorbed topically, so that they are to be administered systemically, and in particular through the oral route.

Systemic administration of such drugs, and, in particular, of acetazolamide, is however affected by a number of side effects, such as a feeling of weariness, gastrointestinal troubles and anorexia, due to the diuretic action of such drugs. Their effects are so severe, especially at the kidney level, that their employment for treating glaucoma is impossible as a matter of fact.

Accordingly, this invention relates to the object of providing novel compounds capable of inhibiting carbonic anhydrase, which compounds, in addition to showing an activity comparable to that of acetazolamide, also are characterized by being well absorbed locally, so that they can be employed by administration through the topical route. It is quite clear that topical administration allows to obtain a therapeutic action without the noxious side effects given by the drug itself when it is administered through the systemic route.

Accordingly, we have devised to modify the molecule of acetazolamide so as to increase both their water solubility and their lipophilic character. As a matter of fact, acetazolamide is practically insoluble and lacks lipophilic groups, its poor absorption when instilled in the eye being ascribable to both such factors.

Accordingly, the present invention provides some compounds related to acetazolamide or to its N-methyl derivatives, which contain a lipophilic acylic chain bearing at its other end an esterified or unesterified carboxylic group, an amino group or a phthalimido group.

Accordingly, the present invention specifically provides compounds related to acetazolamide or to its N-methyl derivatives, capable of inhibiting carbonic anhydrase, said compounds having the formula:

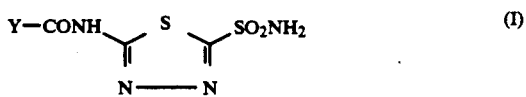

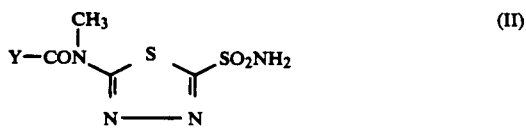

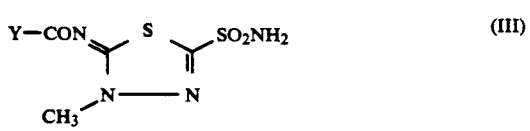

wherein Y is one of the following groups:

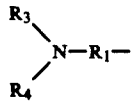

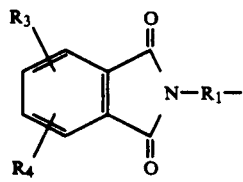

wherein $R_1$ is a straight or branched alkylene or arylalkylene or a phenylene group, $R_2$ is hydrogen or a straight or branched alkyl optionally substituted with halogen, $R_3$ and $R_4$, which are the same or different from one another, are hydrogen or a straight or branched alkyl, as well as the physiologically acceptable salts thereof.

More particularly, the specific objects of the present invention are the compounds having the formulas (I), (II), or (III) wherein Y has one the following structures:

wherein $R_2$ is hydrogen or a straight or branched alkyl having 1-20 carbon atoms and optionally substituted with halogen, n being an integer between 1 and 10; or:

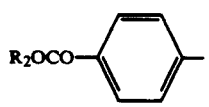

wherein $R_2$ has the same meaning as above; or:

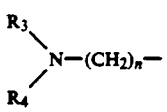

wherein $R_3$ and $R_4$, which are the same or different from one another, are hydrogen or a lower alkyl of 1-6 carbon atoms, n being an integer between 1 and 10; or:

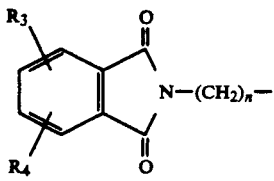

wherein both $R_3$ and $R_4$, as well as n, have the same meanings as above.

The compounds disclosed above can also be in the form of their physiologically acceptable salts, both of bases and of acid, either organic or inorganic.

Examples of suitable bases are sodium hydroxide, potassium hydroxide, calcium, barium and ammonium hydroxides.

Hydrogen halides, sulfonic acid, phosphoric, nitric, perchloric acid, and aliphatic, cycloaliphatic, aromatic or heterocyclic carboxylic and sulfonic organic acids such as formic, acetic, propionic, succinic, glycolic, lactic, malic, tartaric, citric, ascorbic, maleic, hydroxymaleic, piruvic, phenylacetic, benzoic, paraaminobenzoic, anthranilic, p-hydroxybenzoic, salicylic, p-aminosalicylic, pamoic, methansulfonic, ethansulfonic, hydroxyethanesulfonic, ethylensulfonic, halogenobenzensulfonic, toluenesulfonic, naphthalensulfonic, and sulfonylic acid are particularly suitable to form salts for pharmaceutical employment.

The novel active compounds of the present invention keep the property of enzymic inhibitor typical of acetazolamide, and, at the same time, they are more soluble and more lipophilic with respect to acetazolamide because of the presence in their structures of the modifier group Y. Therefore, they are much more absorbable topically.

Moreover, among such compounds those which have in their chain an esterified carboxyl group have a further feature that makes them particularly interesting for topical treatment of glaucoma: due to the action of esterases that are present in the ocular tissue, they give rise to a principal metabolite with a free carboxyl group. The latter, as a result of its physicochemical characteristics, has a poor tendency to pass into the plasma and to spread throughout the organism. This contributes to reduce the possibility that the novel compounds exert a systemic action and hence this contributes to reduce the possibility of occurrence of side effects.

The following table 1 reports some results of in vitro activity tests of the compounds of the present invention; beside the solubility in a buffer at pH=7.6, there is shown the value of the molar concentration that gives a 50% reduction of enzymic activity ($I_{50}$): as can be clearly seen, the in vitro activity of the compounds of the present invention is comparable to or better than that of acetazolamide.

TABLE 1

| COMPOUND | Solubility in buffer pH 7.6 (mg/ml) | $I_{50} \times 10^{-7}$ |
| --- | --- | --- |
| ACETAZOLAMIDE | — | 4.4 |
| RENDE 023 | 0.74 | 5.5 |
| Series I, Y = $CH_3OCO$—$(CH_2)_2$— | | |
| RENDE 024 | 2.25 | 4.5 |
| Series III, Y = $CH_3OCO$—$(CH_2)_2$— | | |
| RENDE 027 | 0.208 | 4.4 |
| Series I, Y = $NH_2$—$(CH_2)_4$— | | |
| RENDE 029 | 2.76 | 7.3 |
| Series I, Y = $CH_3CH_2OCO$—$(CH_2)_2$— | | |
| RENDE 032 | 0.47 | 3.9 |
| Series, I, Y = $CH_3(CH_2)_4OCO$—$(CH_2)_2$— | | |
| RENDE 034 | 1.24 | 3.7 |
| Series I, Y = $(CH_3)_2CHCH_2OCO$—$(CH_2)_2$— | | |
| RENDE 035 | 0.535 | 3.07 |
| Series III, Y = $CH_3(CH_2)_4OCO$—$(CH_2)_2$— | | |
| RENDE 037 | 28.7 | 5.5 |
| Series I, Y = $HOCO$—$(CH_2)_2$— | | |

For determining the in vitro activities, samples were employed at molar concentrations of $10^{-7}$, $3 \times 10^{-7}$, $6 \times 10^{-7}$, and $10^{-6}$, and the results given in Table 1 were obtained by $CO_2$-electrode potentiometric analysis.

In vivo experiments were carried out on the compounds of the present invention, and, amongst the others, those experiments whose results are reported in the following Table 2, concerning the decrease in the ocular pressure in rabbit.

For determining such results a transient ocular hypertension model was employed, said hypertension being obtained in rabbit through rapid venous infusion of suitable volumes (20 ml/kg) of 5% glucose solution.

Albino rabbits from the same farm in New Zealand were employed, whose weights were between 2,500 e 3,000 g. Each treatment was carried out on a group of six animals.

The drug was prepared in a phosphate buffer water solution at pH 7.5. The solution was made isotonic with sodium chloride and the possibility of microbial contamination was prevented through the addition of benzalkonium chloride. In case of compounds of low solubility, a dispersing suspension of the finely divided compound in methyl cellulose was prepared. The solution (or the suspension) was instilled into the right eye of each animal in the amount of 2 drops of 2% solution, at an interval of 2 minutes from one another. The left eye was treated with an equal volume of diluent.

The measurements of pressure were performed while animals were in superficial local anaesthesia (0.4% benoxinate), by means of a McKay-Marg electronic pressure gage, at the times $-30'$, $0'$, $10'$, $20'$, $40'$.

The following table reports the endoocular pressure measured after 10, 20, and 40 minutes both in the right and in the left eye: the higher the difference in the ocular pressure between the treated eye and the untreated eye, the higher the efficiency of the drug considered.

TABLE 2

| Compound | 10' | | 20' | | 40' | |
| --- | --- | --- | --- | --- | --- | --- |
| | OD | OS | OC | OS | OD | OS |
| RENDE 023 | 25.33 | 25.5 | 19.5 | 20.17 | 16.5 | 16.67 |
| RENDE 024 | 24.67 | 25.83 | 20.33 | 21.5 | 17.33 | 17.83 |
| RENDE 027 | 24.0 | 26.17 | 20.83 | 21.5 | 16.83 | 17.33 |
| RENDE 029 | 20.33 | 25.67 | 17.33 | 20.67 | 15.67 | 17.67 |

TABLE 2-continued

| Compound | 10' OD | 10' OS | 20' OC | 20' OS | 40' OD | 40' OS |
|---|---|---|---|---|---|---|
| RENDE 032 | 22.67 | 24.5 | 20.0 | 21.33 | 17.83 | 18.83 |
| RENDE 034 | 21.5 | 25.67 | 19.0 | 21.17 | 16.67 | 17.17 |
| RENDE 035 | 24 | 25.17 | 20.67 | 22.0 | 17.83 | 18.0 |
| RENDE 037 | 19.33 | 26.0 | 17.17 | 21.67 | 15.67 | 19.0 |

The derivatives proposed by the present invention can be employed for pharmaceutical purposes and can be administered topically or systemically as such or in the form of salts. They can be employed not only for the topical or systemic treatment of glaucoma, but also as diuretics, anthypertensive and vasodilating agents.

The products of the present invention and their salts can be employed in the form of pharmaceutical preparations with liquid or solid, organic or inorganic excipients, which are suitable for the topical, oral or parenteral administration. Suitable excipients are pharmaceutically acceptable compounds that do not interfere with the activity of the compounds of this invention, such as water, cellulose, surface active agents, gelatins, lactose, talc, starch, magnesium stearate.

Moreover, the pharmaceutical preparations, which can be collyria, tablets, capsules, pills, solutions, suspensions, emulsions, ointments, creams and suppositories, can also contain preserving agents, as well as stabilizing, wetting, emulsifying, solubilizing agents and salts for adjusting the osmotic pressure and the pH value.

The present invention also relates to some methods for preparing the compounds disclosed above.

A first group comprises methods which, although different in some details depending on the structure of the product to prepare, all start from the 5-amino-2-mercapto-1,3,4-thiadiazole and comprise three fundamental steps: the acylation step of the amino group of the starting compound, the oxidation step of the mercapto group to the corresponding sulfonyl, and the reaction step with ammonia to obtain the corresponding sulfonamide.

The specific method of this group for preparing the compounds of the series I wherein Y is the group $$R_2OCO-R_1-$$

is disclosed with its variants in the following scheme A: 5-amino-2-mercapto-1,3,4-thiadiazole is subjected to acylation (step a), employing as acylating agents the hemiesters of bicarboxylic acids of the formula:

$$R_2OCO-R_1-COOH$$

or the acid halides of said esters having the formula:

$$R_2OCO-R_1-COX$$

wherein X is a halogen atom, or asymmetric diesters of the formula $$R_2OCO-R_1-COOR'$$

or the anhydrides of the hemiesters as above, of the formula:

$$\begin{array}{c} R_2OCO-R_1-CO \\ \phantom{R_2OCO-R_1-C}\diagdown \\ \phantom{R_2OCO-R_1-CO}O \\ \phantom{R_2OCO-R_1-C}\diagup \\ R_2OCO-R_1-CO \end{array}$$

or the cyclic anhydrides of the bicarboxylic acid, of the formula:

$$R_1\begin{array}{c}\diagup CO \\ \phantom{xx}\diagdown \\ \phantom{xx}O \\ \phantom{xx}\diagup \\ \diagdown CO\end{array}$$

In the formulas reported above, $R_2$ is different from hydrogen. In the particular instance in which the final desired product has $R_2=H$, any esterified acylating agent can be employed, and the terminal carboxylic group is liberated at the end of the process, through saponification by prolonged treatment with a strong alkali. In particular, the compound is treated with NaOH for at least 2 hours at room temperature.

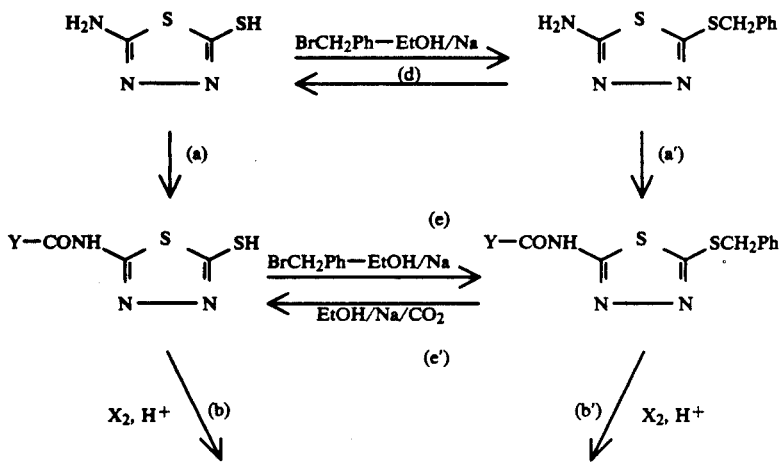

SCHEME A

SCHEME A

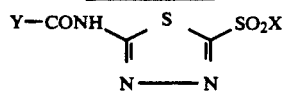

(c) ↓ NH₃ liq.

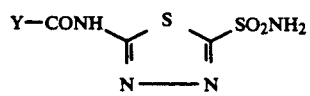

The acylation reaction (a) can be carried out in a suitable organic solvent, preferably in anhydrous tetrahydrofurane (THF) or methylene chloride, under nitrogen at room temperature and employing as a catalyst an organic base, generally triethylamine with small amounts of 4-dimethylaminopyridine (DMAP).

The oxidation of the mercapto group (step b) is performed preferably with a gaseous halide ($X_2$) in acetic acid at low temperature, generally at 0° C.; under these conditions, the sulfonyl halide is formed directly. Such compound, after extraction with an organic solvent or filtration in case it is a solid, is reacted with liquid ammonia (step c).

The reaction step (c) is carried out at a very low temperature, preferably at −78° C., under nitrogen.

The reaction product is purified through direct crystallization or through dissolution in a weak, basic medium and successive precipitation with an acid, preferably with hydrochloric acid at pH 4.

In alternative to the process consisting of the steps (a), (b) and (c), it is possible to protect the mercapto group through benzylation (step d) before performing the acylation of the amino group. Such operation can be carried out, for instance, by reacting the starting compound with benzyl bromide (BrCH₂Ph) in ethanol in the presence of elemental sodium.

After acylation (step a'), the benzyl group can be removed by treatment with elemental sodium in anhydrous ethyl alcohol and bubbling $CO_2$ (step e'). In that case, the preparation process is completed through the steps (b) and (c).

Alternatively, the benzyl derivative is subjected directly to the oxidation of the substituted mercapto group to sulfonyl halide (step b') under conditions similar to those disclosed for the oxidation step (b); the process ends with the step (c).

A further route of synthesis according to the scheme A consists in subjecting the starting compound to acylation (step a), and then performing the benzylation of the mercapto group (step e) followed by the oxidation (step b') and the treatment with ammonia (step c).

Again according to the present invention, the specific process for preparing the compounds of the series I wherein Y is the group

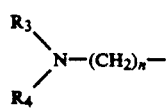

wherein n has the same meaning as in the preceding case, and $R_3$ and $R_4$, which are the same or different from each other, are hydrogen or a straight or branched alkyl chain, is disclosed in the following scheme B: the 5-amino-2-mercapto-1,3,4-thiadiazole is first benzylated in the mercapto group as in the reaction step (d) of the preceding scheme, and then it is subjected to acylation of the amino group with the halogenated carboxylic acid chloride of the formula:

$X—R_1—COCl$ wherein X is a halogen atom and $R_1$ is the chain desired to be present in the final group Y.

SCHEME B

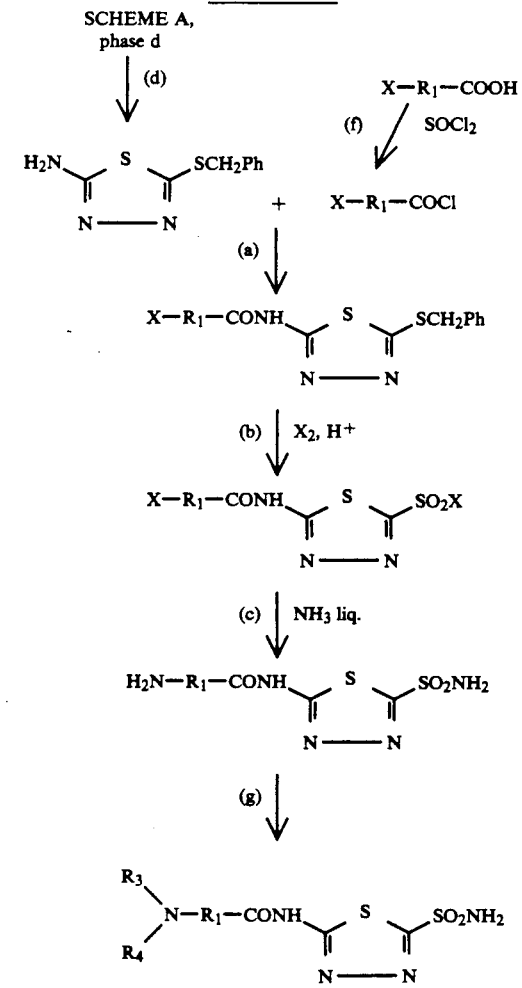

The acylating agent X—R₁COCl can be obtained according to the preparation (step f) by reacting the corresponding halogenated carboxylic acid with thionyl chloride (SOCl₂).

After the acylation step (a) of the benzylated starting compound, which is carried out according to the same operational modes as those employed in (steps a) and (a') of the scheme A, the oxidation step of the mercapto group (step b) is performed, which step is similar to the (step b) of the scheme A.

The compound so obtained, treated with liquid ammonia (step c) as in the (step c) of the scheme A, is subjected to the substitution, both of the halogen atom in the sulfonyl halide group and of the halogen atom bound to $R_1$, with two amino groups.

In case $R_3$ and/or $R_4$ in the desired product are different from hydrogen, the mono-alkylation or di-alkylation of the amino group of Y (step g) is finally performed.

The specific process for producing the compounds of the series I wherein Y is the group

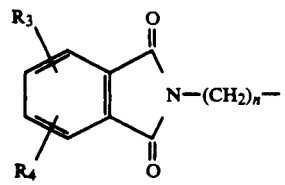

wherein $R_1$, $R_3$, and $R_4$ have the meanings already known, is illustrated with its variants in the following scheme C.

A possible route of synthesis is that of proceeding in the same way as that shown in the scheme B, (steps d), (f) and (a), thus obtaining a benzyl mercaptan which is acylated in the amino group with the chain X—R₁—CO—, and, in a second step, of introducing the phthalimido group as the terminal group in said chain through the reaction with the desired potassium phthalimide (step h).

SCHEME C

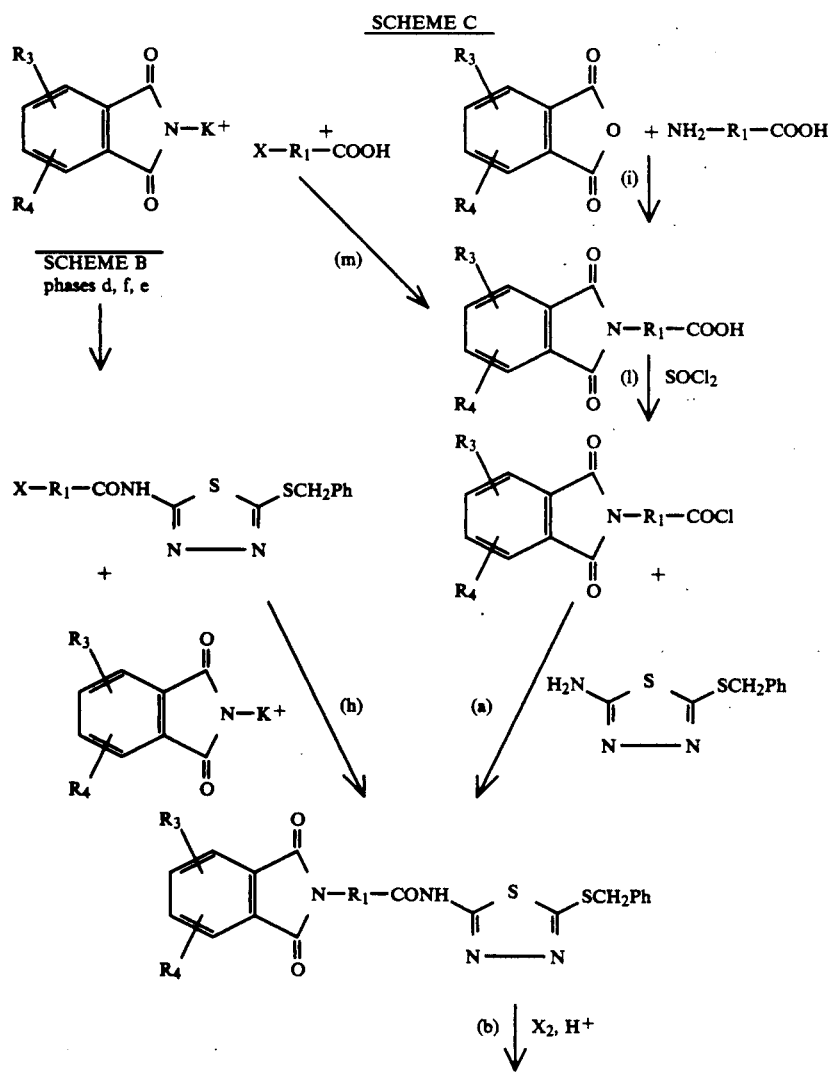

SCHEME C

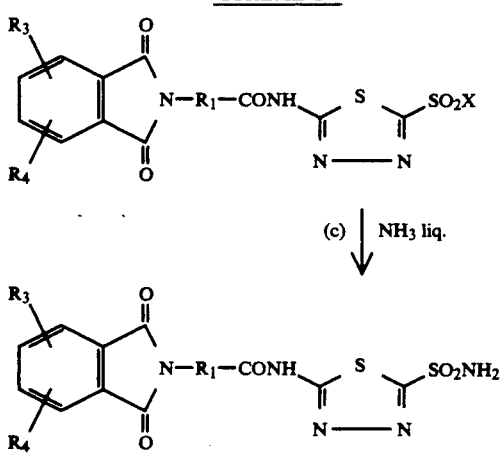

Starting from that point, the oxidation of the benzylmercaptan group and the treatment with ammonia are similar to the steps of the preceding schemes (steps b) and (c).

Alternatively, the phthalimido group can already be present in the initial acylating agent, so that the acylation of the amino nitrogen of the 5-amino-2-benzylmercapto-1,3,4-thiadiazole (step b) is performed according to ways similar to the (steps a) and (a') of the preceding schemes.

The acylating agent of the (step a), which is the phthalimidocarboxylic acid chloride, corresponding to the desired group Y, is obtained (step 1) through treatment of the corresponding carboxylic acid with thionyl chloride; the phthalimidocarboxylic acid can be in turn prepared according to two different ways (step m and step i): either by reaction of potassium phthalimide with a halogenated carboxylic acid of the formula

X—R$_1$—COOH or by reaction of phthalic anhydride with an amino acid of the formula NH$_2$—R$_1$—COOH.

After the acylation (step a), the synthesis proceeds through the same steps as those of the preceding case (steps b and c).

For the preparation of the compounds of the series II and III (the N-methyl derivatives), first of all the acylation is performed of the 5-amino-2-benzylmercapto-1,3,4-thiadiazole (obtained through benzylation according to the (step d) of the Scheme A). According to the desired meaning of the group Y, the scheme A, (steps d) and (a'), or (a) and (e), the scheme B, (steps d) and (a) the scheme C, (step h) or step (a) are followed. The product obtained from such operations can be represented by the following formula:

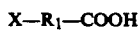

wherein Y' is Y in case the terminal group is an ester or an acid (scheme A) and in case the terminal group is a phthalimido group (scheme C). In case the terminal group is an amino group (scheme B), Y' is X (a halogen), as the amino group will be introduced at the end by means of treatment with ammonia.

The compound of the preceding formula is subjected to a methylation reaction which is pointed out by "n" in the scheme D illustrated below.

SCHEME D

Scheme A, steps d and a' or steps a and e
Scheme B, step a
Scheme C, steps a or h

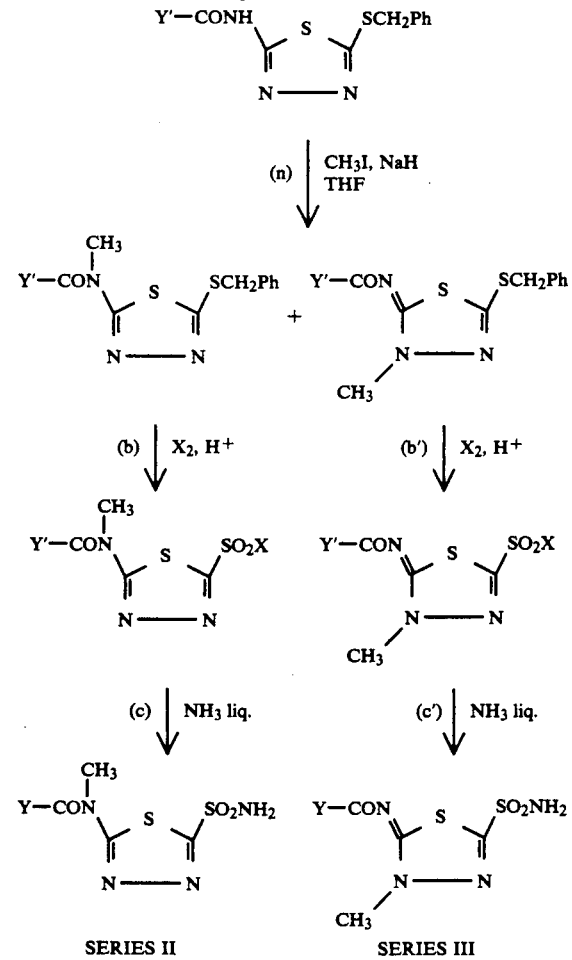

SERIES II                SERIES III

The methylation reaction is performed by dissolving the compound in an anhydrous organic solvent, generally THF, containing sodium hydride in a slight stoichiometric excess.

Then methyl iodide is added while keeping the mixture stirred under nitrogen. After completion of the reaction, the two methyl derivatives are separated by column chromatography.

The two methyl derivatives are then oxidized and transformed into sulfonamide under the same conditions disclosed for the derivatives of the series I (steps b and c, or steps b' and c').

According to a different embodiment of this invention, the compounds of series I in which Y is the group

$R_2OCO—R_1—$ can be prepared by making use of acetazolamide as a starting material, instead of 5-amino-2-mercapto-1,3,4-thiadiazole. In this case acetazolamide is first of all hydrolyzed so as to eliminate the amide group bound in the 5th position and to leave, in place thereof, an amine group. The resulting compound is then acylated in its aminic group, while no transformation is required for the group bound in the 2nd position, which is already the one desired.

The above method is illustrated in the following scheme E: acetazolamide (5-acetamido-2-sulfonamido-1,3,4-thiadiazole) is subjected to acid hydrolysis (step o), followed by neutralization of the resulting acid solution up to precipitation of 5-amino-2-sulfonamido-1,3,4-thiadiazole (step p).

SCHEME E

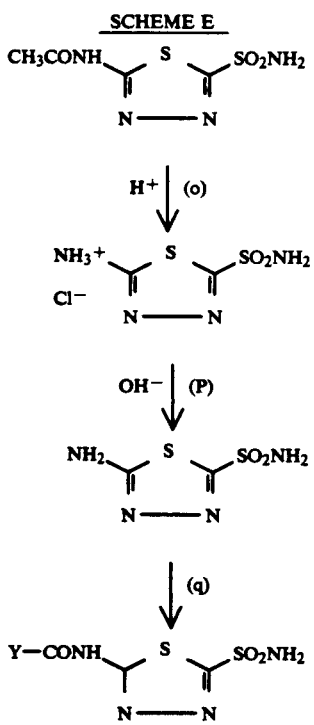

Thereafter, 5-amino-2-solfonamido-1,3,4-thiadiazole is acylated (step q) by means of a hemiester hemialide of the bicarboxylic acid corresponding to the desired group, i.e.

$R_2OCO—R_1—COX$ wherein X is a halogen atom and $R_2$ is different from hydrogen. In the particular case that the final product desired is a free carboxilic acid ($R_2$=H), the process described above is completed by a further step for deblocking the carboxylic group, through a prolonged treatment with a strong alkali.

Other possible acylating agents for carrying out (step q) are the hemiesters of the carboxylic acid at issue, i.e. the compounds of the formula:

$R_2OCO—R_1—COOH$ or their anhydrides:

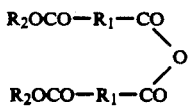

or their cyclic anhydrides of the formula:

or else the corresponding asymmetric diesters:

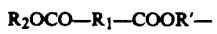
$R_2OCO—R_1—COOR'—$

As already mentioned in the disclosure of the first group of methods according to the invention, the acylation reaction is carried out in anhydrous conditions, into organic solvents such as THF or $CH_2Cl_2$ and under nitrogen, and employing as a catalyst an organic base, preferably triethylamine with a small amount of 4-DMAP.

An example of preparation of an acylating agent wherein X is Cl is the one employing thionyl chloride ($SOCl_2$) for alogenating a hemiester corresponding to the desired group Y, according to the scheme:

$R_2OCO—R_1—COOH + SOCl_2 \rightarrow R_2OCO—R_1—COCl$

The manufacturing process that starts from acetazolamide, compared with the processes first described, has the advantage that it requires, as a starting material, a readily available commercial product of a limited cost, i.e. acetazolamide. Therefore the process can be carried out in a quite simple way. The total yield obtainable is about 40%.

This invention will be disclosed in the following for exemplification and not for limitative purposes, with reference to the following preparative examples.

EXAMPLE 1

5-methylsuccinoylamino-2-sulfonamido-1,3,4-thiadiazole (Rende 023)

Series I, Y=$CH_3OCO(CH_2)_2$— SCHEME A, route steps (a), (b), (c)

(a) Preparation of 5-methylsuccinoylamino-2-mercapto-1,3,4-thiadiazole 5 g of 5-amino-2-mercapto-1,3,4-thiadiazole (0.037 mole) is suspended in 30 ml of $CH_2Cl_2$, under nitrogen at room temperature and with stirring. Then 6 ml of $Et_3N$ (0.043 mole), 5.6 ml (0.037 mole) of succinoyl chloride monomethyl ester and 100 mg of 4-dimethylaminopyridine (4-DMAP) are added. The reaction is checked by thin layer chromatography (TLC) on silica gel (10% methanol in chloroform) and it shows to be complete after 3 hours.

To obtain the purified product, a double volume (about 100 ml) of 30% NH$_4$OH is added to the mixture, then it is diluted with methylene chloride and the water phase, after separation, is acidified to pH 4 with concentrated hydrochloric acid without heating.

The precipitate so formed is filtered off and crystallized from ethanol, yielding 7 g of the product with melting point 183°-186° C.; yield 76%.

$^1$H—NMR 60 MHz (Py): δ=2,8 (m,4H,—CH$_2$CH$_2$—); 3,62 (s,3H,OCH$_3$)

IR(KBr): $\gamma_{max}$=3225, 2920, 1695, 1580, 1365, 990, 730 cm$^{-1}$ (b) Preparation of 
5-methylsuccinoylamino-2-sulfonylchloride-1,3,4-thiadiazole Gaseous chlorine is bubbled through a suspension of 2 g of 5-methylsuccinoylamino-2-mercapto-1,3,4-thiadiazole in 25 ml of a water solution of 33% acetic acid, while the mixture is kept stirred at 0° C. for 2 hours.

The sulfonyl chloride that is precipitated is filtered, then washed with ice-cold water and then dried under vacuum.

2.3 g of sulfonyl chloride is obtained, which is immediately employed for the preparation of the sulfonamide.

(c) Preparation of 
5-methylsuccinoylamino-2-sulfonamido-1,3,4-thiadiazole (Rende 023)

2.3 g of methylsuccinoylamino-2-sulfonylchloride-1,3,4-thiadiazole is slowly added under nitrogen to 50 ml of freshly condensed liquid NH$_3$ at −78° C.

When the addition is complete, ammonia is removed keeping the reaction vessel at room temperature, and the residue is dried in vacuum. The raw product of sulfonamide is then purified through solubilization in 2N NH$_4$OH and subsequent precipitation by addition of concentrated HCl up to pH 4.

After filtering and drying, 1.5 g of the product with melting point 173°-175° C. is obtained, the yield being 60% as calculated starting from 5-methylsuccinoylamino-2-mercapto-1,3,4-thiadiazole.

$^1$H—NMR 300 MHz (DMSO-d$_6$): δ=2,76 (m,4H,—CH$_2$CH$_2$—); 3,59 (s,3H,OCH$_3$); 8,29 (s,2H,SO$_2$NH$_2$)

$^{13}$C—NMR (DMSO-d$_6$): 27,8 (C-9), 29,7 (C-8), 51,5 (CH$_3$), 161 (C-5), 164,2 (CSO$_2$NH$_2$), 171,7 (CONH), 172,8 (CO)

IR (KBr): $\gamma_{max}$ 3320, 3220, 1718, 1700, 1360, 1335, 1160, 925 cm$^{-1}$ Analysis (C$_7$H$_{10}$NO$_5$S$_2$) calcd.: C, 28.56; H, 3.42. N, 19.04; found: C, 28.23; H, 3.45; N, 1879; S, 21.45

EXAMPLE 2

5-methylsuccinoylamino-2-sulfonamido-1,3,4-thiadiazole (Rende 023)

Series I, Y=CH$_3$OCO(CH$_2$)$_2$— SCHEME A, route steps (d), (a'), (b'), (c)

(d) Preparation of 
5-amino-2-benzylmercapto-1,3,4-thiadiazole 10 g of 5-amino-2-benzylmercapto-1,3,4-thiadiazole is added to 300 ml of 95% ethanol into which 1.7 g of sodium had been dissolved. After dissolution of the product, 9 ml of benzyl bromide is added with stirring and at room temperature (molar ratio 1/1). Stirring is ended after 15 minutes, during which period the formation of a white precipitate is observed; the mixture is left standing overnight.

The mixture is then diluted with water and the solid matter is separated by filtration and washed with water. After crystallization from 95% ethanol, 10 g of the product with melting point 158°-161° C. is obtained, the yield being 60%.

(a') Preparation of 
5-methylsuccinoylamino-2-benzylmercapto-1,3,4-thiadiazole 2.7 g (27 mmole) of Et$_3$N, 2.7 g (18 mmole) of succinoyl chloride monomethyl ester and 100 mg of 4-DMAP are successively added to 4 g of 5-amino-2-benzylmercapto-1,3,4-thiadiazole (18 mmole) suspended in 20 ml of anhydrous methyl chloride.

The reaction mixture is kept stirred under nitrogen and is checked by TLC (10% methanol in chloroform); the reaction shows to be complete after 4 hours. The reaction mixture is then diluted with 2N HCl and extracted three times with CH$_2$Cl$_2$. The organic extracts are washed with water till neutral reaction and dried over Na$_2$SO$_4$.

The raw product obtained gives after crystallization from ethanol 4.2 g of the product with melting point 156°-161° C.; yield=70%.

$^1$H—NMR 60 MHz (CDCl$_3$): δ=2,85 (dt,4H,—CH$_2$CH$_2$—); 3,65 (s,3H,OCH$_3$) 4,4 (s,2H,CH$_2$benzyl); 76,3 (s,5H,aryl).

IR (CHCl$_3$): $\gamma_{max}$ 3400, 3170, 2920, 1740, 1700 cm$^{-1}$ (b') and (c) Preparation of 
5-methylsuccinoylamino-2-sulfonamido-1,3,4-thiadiazole (Rende 023)

The oxidation with gaseous chlorine and the subsequent formation of 5-methylsuccinoylamino-2-sulfonamid-1,3,4-thiadiazole are carried out like those performed in Example 1, steps (b) and (c).

EXAMPLE 3

5-methylsuccinoylamino-2-sulfonamido-1,3,4-thiadiazole (Rende 023)

Series I, Y=CH$_3$OCO(CH$_2$)$_2$— SCHEME A, route steps (a), (e), (b'), (c)

(a) Preparation of 
5-methylsuccinoylamino-2-mercapto-1,3,4-thiadiazole

The preparation is carried out as disclosed in Example 1, step (a).

(e) Preparation of 
5-methylsuccinoylamino-2-benzylmercapto-1,3,4-thiadiazole 4 g of 5-methylsuccinoylamino-2-mercapto-1,3,4-thiadiazole is added to 420 mg of sodium dissolved in 80 ml of 95% ethanol. After dissolution of the product, 22 ml of benzyl bromide is added with stirring at room temperature. The reaction mixture is kept in such conditions for 15 minutes, during which time the formation of a white precipitate is observed. Stirring is then stopped and the mixture is kept reacting overnight. Then the same is diluted with water, filtered and washed with water. The solid product so obtained is purified through crystallization from ethanol so as to obtain 5.2 g of benzylate; yield=86%.

(b) and (c) Preparation of the 5-methylsuccinoylamino-2-sulfonamido-1,3,4-thiadiazole (Rende 023)

The process is carried out according to the steps (b') and (c) of the preceding Example.

EXAMPLE 4

5-methylsuccinoylamino-2-sulfonamido-1,3,4-thiadiazole (Rende 023)

Series I, Y=CH$_3$OCO(CH$_2$)$_2$— SCHEME A, route steps (d), (a'), (e'), (b), (c)

(d) and (a') Preparation of 5-methylsuccinoylamino-2-benzylmercapto-1,3,4-thiadiazole The process is carried out according to steps (d) and (a') of Example 2.

(e') Debenzylation of 5-methylsuccinoylamino-2-benzylmercapto-1,3,4-thiadiazole 1 g of the benzylate dissolved in 100 ml of absolute EtOH is added to 7.5 g of sodium. The mixture is kept under reflux till complete dissolution of sodium. A further volume of 300 ml of ethanol is then added, and CO$_2$ is bubbled for 1¼ hours. Sodium carbonate so formed is filtered off and repeatedly washed with ethanol.

Washing and filtering waters are collected and then concentrated in vacuum under CO$_2$, and the residue is extracted three times with ethyl acetate.

After solvent removal, the raw product so obtained is crystallized from ethanol yielding 440 mg of 5-methylsuccinoylamino-2-mercapto-1,3,4-thiadiazole; yield=70%.

(b) and (c) Preparation of 5-methylsuccinoylamino-2-sulfonamido-1,3,4-thiadiazole (Rende 023)

The process is carried out according to the steps (b) and (c) of Example 1.

EXAMPLE 5

5-succinoylamino-2-sulfonamido-1,3,4-thiadiazolic acid (Rende 037)

Series I; Y=HOCO(CH$_2$)$_2$— SCHEME A

Preparation of 5-methylsuccinoylamino-2-sulfonamid-1,3,4-thiadiazole (Rende 023)

The preparation is carried out according to the procedures disclosed in any one of the preceding examples.

Preparation of 5-succinoylamino-2-sulfonamido-1,3,4-thiadiazolic acid (Rende 037)

5 g of 5-methylsuccinoylamino-2-sulfonamido-1,3,4-thiadiazole is dissolved into 20 ml of 5N NaOH and kept standing for 2 hours at room temperature. The solution is acidified to pH 4 by adding concentrated HCl. The solid so formed is filtered off, washed with cold water and then dried. 3.3 g of the acid is obtained with melting point 196°-198° C. and yield of 70%.

$^1$H—NMR 300 MHz (DMSO-d$_6$): δ=2,68 (dt,4H,—CH$_2$CH$_2$—); 8,3 (s,2H,SO$_2$NH$_2$); 12,7 (s',1H,OH)

$^{13}$C—NMR (DMSO-d$_6$): 27,8(C-9), 2.95(C-8); 160,6(C-5); 163,7(CSO$_2$NH$_2$); 171(CONH); 172,9(CO)

IR (KBr): γ$_{max}$ 3520, 3220, 1732, 1723, 1370, 1170 cm$^{-1}$

Elemental analysis (C$_6$H$_8$N$_4$O$_5$S$_2$) Calcd.: C, 25.7; H, 2.9, N, 19.98; S, 22.88; Found: C, 25.3; H, 3.15, N, 19.62; S, 22.50.

EXAMPLE 6

5-Ethylsuccinoylamino-2-sulfonamido-1,3,4-thiadiazole (Rende 029)

Series I, Y=CH$_3$CH$_2$OCO(CH$_2$)$_2$— SCHEME A, route steps (d), (a'), (b'), (c)

Preparation of succinoyl chloride monoethyl ester (the acylating agent)

35 ml of absolute ethanol and a catalytic amount (0.05 ml) of concentrated sulfuric acid are added to 5 g of succinic anhydride. The reaction mixture is kept under reflux for 30 minutes, then it is stirred for 20 minutes at room temperature and again for 30 minutes by heating.

The excess ethanol is evaporated and the solution is diluted with water and then extracted with acetate. The organic extracts are washed with brine, then dried over Na$_2$SO$_4$ so giving, after solvent evaporation, an amount of 6.3 g of succinic acid monoethyl ester.

6.3 g of the acid is kept under reflux for 3 hours at 60° C. with 4.7 ml of SOCl$_2$ (molar ratio 1:1.5).

The solution is distilled under reduced pressure (18 mm Hg) so obtaining 4.4 g of the product (boiling point=93° C., 18 mm Hg).

(d) Preparation of 5-amino-2-benzylmercapto-1,3,4-thiadiazole

The process is carried out according to the step (d) of Example 2.

(a') Preparation of 5-ethylsuccinoylamino-2-benzylmercapto-1,3,4-thiadiazole 4.4 ml (30 mmole) of triethylamine, 3.3 g of succinoyl chloride monoethyl ester (20 mmole) and 100 mg of 4-dimethylaminopyridine are successively added to 4.5 g of 5-amino-2-benzylmercapto-1,3,4-thiadiazole (20 mmole) suspended in 10 ml of anhydrous methylene chloride. The reaction mixture is kept stirred under a nitrogen and a TLC is performed to follow the reaction course (5% methanol in chloroform), said reaction showing to be complete in 6 hours. The mixture is then filtered, diluted with 0.2N HCl and extracted three times with methylene chloride. The organic extracts are then collected, washed with water till neutrality and finally dried over anhydrous sodium sulfate. The raw product so obtained is purified by crystallization from ethanol so giving 4.9 g of the product with melting point 140°-143° C. and yield of 70%.

$^1$H—NMR 60 MHz (DCl$_3$): δ=1,2 (t,3H,CH$_3$); 2,88 (m,4H,—CH$_2$CH$_2$—); 4,1 (q,2H,OCH$_2$); 4,5 (s,2H,CH$_2$benzyl); 7,34 (s,5H,aryl)

IR (CHCl$_3$): γ$_{max}$ 3165, 2920, 1735, 1700, 1555, 1310, 1160 cm$^{-1}$ (b') Preparation of
5-ethylsuccinoylamino-2-sulfonylchloride-1,3,4-thiadiazole 4 g of 5-ethylsuccinoylamino-2-benzylmercapto-1,3,4-thiadiazole is suspended in 70 ml of a 33% water solution of acetic acid. The mixture is kept stirred at 10° C. under chlorine for three hours and a half.

The solid chloride so formed is filtered off in vacuo and then washed with cold water and set aside to dry. 3.4 g of the raw product is thus obtained, and it is immediately employed for the next reaction.

(c) Preparation of
5-ethylsuccinoylamino-2-sulfonamide-1,3,4-thiadiazole
(Rende 029)

3.4 g of 5-ethylsuccinoylamino-2-sulfonylchloride-1,3,4-thiadiazole is added at −78° C. under nitrogen atmosphere to 80 ml of freshly condensed liquid ammonia. The reaction vessel is then placed in a water bath and ammonia is thus removed with a nitrogen stream.

The solid residue is purified by direct crystallization with 95% ethanol (checks performed through TLC with 6% methanol in chloroform, RF about 0.4). 1.7 g of the product is obtained with melting point 192°-197° C. and 50% yield starting from 5-ethylsuccinoylamino-2-benzylmercapto-1,3,4-thiadiazole.

$^1$H—NMR 300 MHz (DMSO-d$_6$): δ=1,15 (t,3H,CH$_3$); 2,68 (t,2H,CH$_2$); 2,79 (t,2H,CH$_2$); 4,05 (q,2H,OCH$_2$); 8,35 (s,2H,SO$_2$NH$_2$)

$^{13}$C—NMR (DMSO-d$_6$): 14(CH$_3$); 28,1(C-9); 29,7(C-8); 60(C-11); 161(C-5); 164,2(CSO$_2$NH$_2$); 171,2(CONH); 171,8(C-10)

IR (KBr): $\gamma_{max}$ 3330, 1720, 1555, 1340, 1170, 930 cm$^{-1}$

Elemental analysis (C$_8$H$_{12}$N$_4$O$_5$S$_2$) Calcd.: C, 31.16, H, 3.92, N, 18.07, S, 20.79; Found: C, 31.51, H, 4.1, N, 17.94, S, 20.44.

EXAMPLE 7

5-Pentylsuccinoylamino-2-sulfonamido-1,3,4-thiadiazole (Rende 032)

Series I, Y=CH$_3$(CH$_2$)$_4$OCO(CH$_2$)$_2$— SCHEME A, route steps (d), (a'), (b'), (c)

Preparation of succinoyl chloride monopentyl ester (the acylating agent)

5.4 ml of 1-pentanol (molar ratio 1:1) and 0.1 ml of concentrated sulfuric acid are added to 5 g of succinic anhydride. The reaction mixture is kept under reflux at 70° C. for 15 minutes, then it is stirred at room temperature for 15 minutes and it is heated again for 30 minutes.

The excess alcohol is evaporated in vacuo and the reaction mixture is then diluted with water and extracted with ethyl acetate. The organic extracts, after drying over anhydrous sodium sulfate and evaporation, yield 7.2 g of the succinic acid monopentyl ester.

The hemiester so obtained is chlorinated by treatment with 4.1 ml of SOCl$_2$ (molar ratio 1:1.5) under reflux at 70° C. for 5 hours.

The chloride so formed is then distilled under reduced pressure and 6.7 of the chloride is collected.

(d) Preparation of
5-amino-2-benzylmercapto-1,3,4-thiadiazole

The preparation is carried out according to the step (d) of Example 2.

(a') Preparation of
5-pentylsuccinoylamino-2-benzylmercapto-1,3,4-thiadiazole 4.6 ml (34 mmole) of triethylamine, 4.6 ml of succinoyl chloride monopentyl ester and 150 mg of 4-DMAP are successively added to 5 g of 5-amino-2-benzylmercapto-1,3,4-thiadiazole (22 mmole) suspended in 30 ml of anhydrous CH$_2$Cl$_2$.

The mixture is kept stirred at room temperature under inert gas atmosphere for 5 hours and the reaction is checked through TLC (6% methanol in chloroform).

The reaction mixture is neutralized with 2N HCl and is extracted three times with methylene chloride; the organic extracts are washed with water and then they are dried over anhydrous sodium sulfate.

The raw product so obtained is purified by crystallization from ethanol so giving 5.3 g of the product with melting point 128°-130° C. and yield of 60%.

$^1$H—NMR 60 MHz (CDCl$_3$): δ=0,83 (t,3H, CH$_3$); 1,32 [m,6H, (CH$_2$)$_3$]; 2,8-(m,4H,—CH$_2$CH$_2$—); 4,01 (t,2H,OCH$_2$); 4,35 (s,2H,CH$_2$benzyl); 7,32 (s,5H, aryl)

IR (CHCl$_3$): $\gamma_{max}$ 3160, 2925, 1730, 1700, 1505, 1300, 1160 cm$^{-1}$ (b') Preparation of
5-pentylsuccinoylamino-2-sulfonylchloride-1,3,4-thiadiazole 5 g of 5-pentylsuccinoylamino-2-benzylmercapto-1,3,4-thiadiazole is suspended in 80 ml of a 33% water solution of acetic acid. The mixture is kept stirred at 0° C. with a constant chlorine flow for 4 hours. The solid chloride so formed is filtered off, washed with cold water and then set aside to dry.

3.5 g of the sulfonyl chloride is so obtained, and it is immediately employed for preparing the sulfonamide.

(c) Preparation of
5-pentylsuccinoylamino-2-sulfonamido-1,3,4-thiadiazole (Rende 032)

3.5 g of 5-pentylsuccinoylamino-2-sulfonylchloride-1,3,4-thiadiazole is added at −78° C. under nitrogen to 80 ml of freshly condensed liquid ammonia.

The ammonia is removed with a nitrogen stream by dipping the flask into a water bath, and the residue is purified through solubilization into 2N NH$_4$OH (pH 8) and then through precipitation of the product by adding concentrated HCl till reaching a pH 4. After filtration and drying, 2.2 g of the sulfonamide is obtained with melting point 201°-203° C. and 48% yield starting from 5-pentylsuccinoyl amino-2-benzylmercapto-1,34-thiadiazole.

$^1$H—NMR 300 MHz (DMSO-d$_6$): δ=0,80 (t,3H,CH$_3$); 1,2 (s,4H,(CH$_2$)$_2$pent); 1,55 (t,2H,OCH$_2$—CH$_2$); 2,75(dt,4H,—CH$_2$CH$_2$—); 4,0 (t,2H,OCH$_2$); 8,4 (s,2H,SO$_2$NH$_2$)

$^{13}$C—NMR (DMSO-d$_6$): 13,7(CH$_3$), 21,7(C-14), 27,5(C-12), 28(C-9), 28,1(C-13), 29,8(C-8), 64(C-11), 161(C-5), 164,2(CSO$_2$NH$_2$), 171,2(CONH), 171,8(CO)

Elemental analysis (C$_{11}$H$_{18}$N$_4$O$_5$S$_2$) Calcd.: C, 37.7; H, 5.18; N, 15.99; S, 18.3; Found: C, 38.05; H, 5.27; N, 16.01; S, 18.10.

IR (KBr): $\gamma_{max}$ 3340, 3240, 1720, 1710, 1550, 1365, 1165, 930 cm$^{-1}$

EXAMPLE 8

5-Isobutylsuccinoylamino-2-sulfonamido-1,3,4-thiadiazole (Rende 034)

Series I, Y=(CH$_3$)$_2$CHCH$_2$OCO(CH$_2$)$_2$—SCHEME A, route steps (d), (a'), (b'), (c)

Preparation of succinoyl chloride monoisobutyl ester (the acylating agent)

5.5 ml of isobutyl alcohol is added to 5 g of succinic anhydride (molar ratio 1:1.2) together with 0.05 ml of concentrated sulfuric acid.

The reaction mixture is kept under reflux at 60° C. for 30 minutes and then it is stirred at room temperature for 20' and then again under reflux for a further time of 30 minutes. The excess alcohol is removed in vacuo and the mixture is diluted with water and extracted with ethyl acetate. The organic phase after drying over sodium sulfate gives 6.5 g of succinic acid monoisobutyl ester that is kept then under reflux with 4 ml of SOCl$_2$ at 60° C.

The mixture yields, after distillation under reduced pressure, 6.4 g of the product.

(d) Preparation of 5-amino-2-benzylmercapto-1,3,4-thiadiazole

The process is carried out according to the step (d) of Example 2

(a') Preparation of 5-isobutylsuccinoylamino-2-benzylmercapto-1,3,4-thiadiazole 2.9 ml (22 mmole) of Et$_3$N, 2.8 g (14 mmole) of succinoyl chloride monoisobutyl ester and 90 mg of 4-DMAP are successively added to 3.2 g (14 mmole) of 5-amino-2-benzylmercapto-1,3,4-thiadiazole suspended in 10 ml of anhydrous CH$_2$Cl$_2$.

The reaction mixture is kept under nitrogen and the reaction course is checked through TLC (6% methanol in chloroform); the reaction shows complete in 5 hours.

The mixture is then neutralized with 0.1N HCl (5 ml) and is extracted twice with 50 ml portions of CH$_2$Cl$_2$. The organic extracts are then washed with water and dried over sodium sulfate.

After crystallization from ethanol, 2.7 g of the product is obtained with melting point 133°-136° C. and 50% yield.

$^1$H—NMR 60 MHz (CDCl$_3$): δ=0,85 (d,6H,CH$_3$); 1,9 (m,1H,CH); 2,9 (m,4H, —CH$_2$CH$_2$—); 3,8 (d,2H,OCH$_2$); 4,35 (s,2H,CH$_2$benzyl); 7,3 (s,5H,aryl)
IR (CHCl$_3$): $\gamma_{max}$ 3400, 3160, 2940, 1730, 1700, 1555, 1305, 1160 cm$^{-1}$

(b') Preparation of 5-isobutylsuccinoylamino-2-sulfonylchloride-1,3,4-thiadiazole 2 g of 5-isobutylsuccinoylamino-2-benzylmercapto-1,3,4-thiadiazole suspended in 20 ml of a 33% water solution of acetic acid is kept stirred at 0° C. under chlorine for 3 hours.

The sulfonyl chloride product so formed is then filtered off, washed with water and set aside to dry in vacuo.

1.74 g of the product is thus obtained which is employed for the next reaction.

(c) Preparation of 5-isobutylsuccinoylamino-2-sulfonamide-1,3,4-thiadiazole (Rende 034)

1.74 g of 5-isobutylsuccinoylamino-2-sulfonylchloride 1,3,4-thiadiazole is slowly added under nitrogen to 35 ml of freshly condensed liquid ammonia at −78° C.

When the addition has been completed, the ammonia is removed keeping the reaction flask at room temperature and keeping the nitrogen flow. The raw product so obtained is purified by solubilization in 2N NH$_4$OH at pH 8.5 and subsequent precipitation of sulfonamide by addition of concentrated HCl till reaching pH 4.

After filtration and drying, 1.5 g of the product is obtained with melting point 201°-203° C. and 85% yield starting from the benzylated compound.

$^1$H—NMR (300 MHz) (DMSO-d$_6$): δ=0,85 (d,6H,CH$_3$); 1,85 (m,1H,CH); 2,7 (t,2H,CH$_2$); 2,82 (t,2H,CH$_2$); 3,81 (d,2H,OCH$_2$)
$^{13}$C (DMSO-d$_6$): 18,7(2CH$_3$): 27,1(C-12); 28,1(C-9); 29,8(C-8); 69,8(C-11), 161(C-5); 164,2(CSO$_2$NH$_2$); 171,2(CONH); 171,7(CO)

Elemental analysis (C$_{10}$H$_{16}$N$_4$O$_5$S$_2$) Calcd.: C, 35.7; H, 4.79; N, 16.65; S, 19.06; Found: C, 35.84; H, 4.86; N, 16.80; S, 18.98.

IR (KBr): $\gamma_{max}$ 3315, 3225, 2980, 1740, 1700, 1555, 1370, 1175, 920 cm$^{-1}$

EXAMPLE 9

5-Dodecylsuccinoylamino-2-sulfonamido-1,3,4-thiadiazole (Rende 033)

Series I, Y=CH$_3$(CH$_2$)$_{11}$CO(CH$_2$)$_2$— SCHEME A, route steps (d), (a'), (b'), (c)

Preparation of succinoyl chloride monododecyl ester (the acylating agent)

11.2 ml of 1-dodecyl alcohol is added to 5 g of succinic anhydride (molar ratio 1:1) together with 0.05 ml of concentrated sulfuric acid. The reaction mixture is kept under reflux at 70° C. for 15 minutes, then it is stirred at room temperature for 15 minutes and again heated for 30 minutes.

The excess alcohol is removed by evaporation in vacuum and the mixture is diluted with water and extracted with ethyl acetate.

The organic extracts, after drying over anhydrous sodium sulfate and removal of the solvent through evaporation, yield 9.7 g of the succinic acid monododecyl ester.

The monoester product so obtained is then reacted with 3.7 ml of SOCl$_2$ (molar ratio 1:1.5) under reflux at 65° C. for 4 hours.

The excess unreacted SOCl$_2$ is removed by distillation from the solution so obtained under reduced pressure, and the amount of 8.2 g of the residue is made up of the solid succinoyl chloride monododecyl ester with melting point 104°-106° C.; the yield of the whole process is 54%.

(d) Preparation of 5-aminobenzylmercapto-1,3,4-thiadiazole

The process is carried out according to the step (d) of Example 2.

(a') Preparation of 5-dodecylsuccinoylamino-2-benzylmercapto-1,3,4-thiadiazole 3.4 ml (25 mmole) of $Et_3N$, 5 g (16 mmole) of succinoyl chloride monododecyl ester and 80 mg of 4-DMAP are successively added to 3.7 g (16 mmole) of 5-amino-2-benzylmercapto-1,3,4-thiadiazole suspended in 25 of anhydrous methylene chloride.

The mixture is kept stirred under nitrogen atmosphere and the reaction course is checked through TLC (5% methanol in chloroform) and the reaction shows to be complete in 6 hours.

The reaction mixture is neutralized with 2N HCl and extracted twice with $CH_2Cl_2$. The organic extracts are then washed with water and dried over anhydrous sodium sulfate.

The raw product so obtained, after crystallization from ethanol, gives 4.4 g of the product with melting point 130°–133° C., and 55% yield.

$^1H$—NMR 60 MHz ($CDCl_3$): $\delta = 0.85$ (t,3H,$CH_3$); 1,3 (s,20H,($CH_2$)$_{10}$); 2,9 (m,4H,—$CH_2CH_2$—); 4,1 (t,2H,$OCH_2$); 4,35 (s,2H,$CH_2$benzyl); 7,25 (s,5H,aryl)
IR ($CHCl_3$): $\gamma_{max}$ 3400, 3165, 2920, 1732, 1700 cm$^{-1}$

(b') Preparation of 5-dodecylsuccinoylamino-2-sulfonilchloride-1,3,4-thiadiazole Chlorine is bubbled through a suspension of 4 g of 5-dodecylsuccinoylamino-2-benzylmercapto-1,3,4-thiadiazole in 40 ml of a 33% acetic acid solution, while the mixture is kept stirred at 5° C. for 2 hours.

The solid sulfonyl chloride is filtered off, washed with ice-cold water and then dried in vacuo.

3.5 g of the product is obtained which is immediately employed for preparing sulfonamide.

(c) Preparation of 5-dodecylsuccinoylamino-2-sulfonamido-1,3,4-thiadiazole (Rende 033).

3.5 g of 5-dodecylsuccinoylamino-2-sulfonilchloride-1,3,4-thiadiazole is slowly added under nitrogen atmosphere to 60 ml of freshly condensed liquid $NH_3$.

When the addition is complete, ammonia is removed by leaving the reaction vessel at room temperature and bubbling through the mixture a stream of nitrogen, and the raw product is checked through TLC (8% methanol in chloroform). Sulfonamide is directly crystallized from ethanol, so yielding 2.5 g of a product with melting point 184°–186° C. and 70% yield starting from 5-dodecylsuccinoylamino-2-benzylmercapto-1,3,4-thiadiazole.

$^1H$—NMR 300 MHz (DMSO-$d_6$): $\delta = 0.85$ (t,3H,$CH_3$); 1,25 (m,20H,($CH_2$)$_{10}$; 2,65 (t,2H,—$CH_2CO$); 2,8 (t,2H,$COCH_2$); 4,0 (t,2H,$OCH_2$); 8,32 (s',2H,$SO_2NH_2$)

$^{13}C$—NMR (DMSO-$d_6$): 13,3($CH_3$); 28,1(C-9); 29,8(C-8); 64(C-11); 161(C-5), 164,2($CSO_2NH_2$); 171,2($CONH$); 171,8(CO)

Analysis ($C_{18}H_{32}N_4O_5S_2$) calcd.: C, 48.19; H, 7.19; N, 12.49; S, 14.29; found: C, 49.07; H, 7.6; N, 12.02; S, 15.67.

IR (KBr): $\gamma_{max}$ 3325, 3240, 2920, 1740, 1720, 1470, 1175, 940 cm$^{-1}$

5-Methylglutaroylamino-2-sulfonamido-1,3,4-thiadiazole (Rende 030)

Series I, Y=$CH_3OCO(CH_2)_3$ SCHEME A, route steps (d), (a'), (b'), (c)

(d) Preparation of 5-amino 2-benzylmercapto-1,3,4-thiadiazole

The process is carried out according to step (d) of Example 2.

(a') Preparation of 5-methylglutaroylamino-2-benzylmercapto-1,3,4-thiadiazole 1.9 ml (13 mmole) of $Et_3N$, 1.26 ml (9 mmole) of glutaroyl chloride monomethyl ester and 100 mg of 4-DMAP are succesively added to 2 g (9 mmole) of 5-amino-2-benzylmercapto-1,3,4-thiadiazole suspended in 12 ml of anhydrous $CH_2Cl_2$. The mixture is kept stirred at room temperature under an inert.

The reaction is checked through TLC (6% methanol in chloroform) and it shows complete within 2 hours. The reaction mixture is then neutralized with 2N HCl and extracted twice with $CH_2Cl_2$; the organic extracts are then washed with water and dried over anhydrous sodium sulfate.

The raw product so obtained is purifies through crystallization from ethanol so yielding 3.02 g of the product with melting point 121°–123° C. and 96% yield.

$^1H$—NMR 60MHz ($CDCl_3$): $\delta = 1,9$ (m,2H,—$CH_2$—); 2,5 (m,4H,($CH_2$)$_2$); 3,5 (s,3H,$OCH_3$); 4,3(s,2H,$CH_2$benzyl); 7,3 (s,5H,aryl)
IR ($CHCl_3$): $\gamma_{max}$ 3400, 3160, 2950, 1735, 1700, 1555, 1300 cm$^{-1}$

(b') Preparation of 5-methylglutaroylamino-2-sulfonylchloride-1,3,4-thiadiazole 3 g of 5-methylglutaroylamino-2-benzylmercapto-1,3,4-thiadiazole is suspended in 50 ml of a 33% water solution of acetic acid, and the mixture is kept stirred at 0° C. with bubbling a constant stream of chlorine.

The disappearance of the starting product is checked through TLC (4% methanol in chloroform) and it is shown complete within 2 hours.

The chloride so formed is filtered off, washed with cold water and dried in vacuo.

2.4 g of sulfonyl chloride is obtained which is immediately employed for the preparation of sulfonamide.

(c) Preparation of 5-methylglutaroylamino-2-sulfonamido 1,3,4-thiadiazole (Rende 030)

2.4 g of sulfonyl chloride is slowly added under nitrogen atmosphere into 50 ml of freshly condensed liquid ammonia, at −78° C. When the addition is complete, ammonia is removed by leaving the reaction flask at room temperature, and the residue is dried in vacuo.

The raw sulfonamide is purified through dissolution in 2N $NH_4OH$ at pH 8, and successive precipitation by addition of conc. HCl till pH 4.

After filtering and drying, 1.85 g of sulfonamide is obtained with melting point 181°–184° C. and 70% yield starting from benzylthiol.

$^1H$—NMR 300MHz (DMSO-$d_6$): $\delta = 1,85$ (m,2H,$CH_2$—); 2,4 (t,2H,$CH_2$); 2,55 (t,2H,$CH_2$); 3,6 (s,3H,$OCH_3$); 8,3 (s,2H,$SO_2NH_2$)

$^{13}$C—NMR (DMSO-d$_6$): 19,6(C-9); 32,3(C-10), 33,7(C-8); 51,2(C-12); 161(C-5); 164,2(CSO$_2$NH$_2$); 171,6(CONH); 172,8(CO)

Analysis (C$_8$H$_{12}$N$_4$O$_5$S$_2$) calcd. C, 31.16; H, 3.92; N, 18.07; S, 20.79; Found: C, 31.36; H, 3.99; N, 18.43; S, 20.51.

IR (KBr): $\gamma_{max}$ 3400, 3145, 2920, 1735, 1680, 1380, 1300, 1170 cm$^{-1}$

EXAMPLE 11

5-Trifluoroethylsuccinoylamino-sulfonamido-1,3,4-thiadiazole (Rende 039)

Series I, Y=CF$_3$CH$_3$OCO(CH$_2$)$_2$— SCHEME A, route steps (d), (a'), (b'), (c)

Preparation of succinoyl chloride monotrifluoroethyl ester (the acylating agent)

3.59 ml of CF$_3$CH$_2$OH and 0.05 ml of conc. sulfuric acid are added to 5 g of succinic anhydride.

The reaction mixture is kept under reflux at 70° C. for 30 minutes, then for 20 minutes under stirring at room temperature, and again heated for 30 minutes.

The excess alcohol is evaporated and the solution is diluted with water and extracted with acetate.

The organic extracts are then washed with brine, and then dried over sodium sulfate so giving, after evaporation of the solvent, 7.3 g of the succinic acid monotrifluoroethyl ester.

7.3 g of the acid is then treated under reflux for 5 hours at 70° C. with 4 ml of SOCl$_2$ (molar ratio 1/1.5).

The solution is distilled under reduced pressure so giving 5.5 g of the product.

(d) Preparation of 5-amino-2-benzylmercapto-1,3,4-thiadiazole

The process is carried out according to step (d) of Example 2.

(a') Preparation of 5-trifluoromethylsuccinoylamino-2-benzylmercapto-1,3,4-thiadiazole 5.26 ml (38 mmole) of triethylamine, 5.5 g of succinoyl chloride monotrifluoroethyl ester (25 mmole) and 120 mg of 4-DMAP are successively added to 5.6 g of 5-amino-2-benzylmercapto-1,3,4-thiadiazole (25 mmole) suspended in 37 ml of anhydrous CH$_2$Cl$_2$.

The reaction mixture is kept stirred under nitrogen atmosphere and the reaction course is checked through TLC (5% methanol in chloroform), the reaction being complete within 4 hours.

The reaction mixture is filtered, then diluted with 0.2N HCl and extracted three times with methylene chloride. The organic extracts are then collected together and washed with water, and then they are dried over anhydrous sodium sulfate. The raw product so obtained is purified through crystallization from ethanol so giving 7.46 g of the product with melting point 169°-173° C. and 73% yield.

$^1$H—NMR 80 MHz (DMSO-d$_6$): δ=2,6 (s,4H,—CH$_2$CH$_2$—); 4,4 (s,2H,CH$_2$benzyl); 4,7 (q,2H,OCH$_2$); 7,4 (s,5H,aryl)

IR (CHCl$_3$): $\gamma_{max}$ 3160, 2950, 1730, 1710, 1300, 1150 cm$^{-1}$

(b') Preparation of 5-trifluoroethylsuccinoylamino-2-sulfonylchloride-1,3,4-thiadiazole 5 g of 5-trifluoroethylsuccinoylamino-2-benzylmercapto-1,3,4-thiadiazole is suspended in 70 ml of a 33% acetic acid water solution. The mixture is kept stirred at 5° C. under chlorine atmosphere for 4 hours. The solid chloride so formed is filtered in vacuo, washed with cold water and dried. 2.6 g of the raw product is obtained which is immediately employed for the subsequent reaction.

(c) Preparation of 5-trifluoroethylsuccinoylamino-2-sulfonamido-1,3,4-thiadiazole (Rende 039)

2.6 g of 5-trifluoroethylsuccinoylamino-2-sulfonylchloride-1,3,4-thiadiazole is added to 60 ml of freshly condensed liquid ammonia at −78° C. under nitrogen atmosphere. When the addition is complete, ammonia is removed with a nitrogen stream while the reaction vessel is kept within a water bath.

The residue so obtained is not identified as the compound shows to be very unstable and becomes very easily hydrolysed.

EXAMPLE 12

5-(5-Aminovaleroylamino)-2-sulfonamido-1,3,4-thiadiazole (Rende 027)

Series I, Y=NH$_2$(CH$_2$)$_4$— SCHEME B

(c) Preparation of 5-chlorovaleroylamino-2-benzylmercapto-1,3,4-thiadiazole 1.5 ml (13 mmole) of Et$_3$N, 1.38 g of 5-chlorovaleroyl chloride and 80 ml of 4-DMAP are successively added to 2 g of 5-amino-2-benzylmercapto-1,3,4-thiadiazole (8.9 mmole) suspended in 5 ml of anhydrous methylene chloride at room temperature with stirring and under nitrogen atmosphere. The reaction is checked by TLC (10% methanol in chloroform) and it is complete after 3 hours. The solid product so formed is filtered, washed with water and purified by crystallization from ethanol. 2.7 g of 5-chlorovaleroylamino-2-benzylmercapto-1,3,4-thiadiazole is obtained with melting point 145°-148° C. and 90% yield.

$^1$H—NMR 60 MHz (CDCl$_3$): δ=1,9 (m,4H,—CH$_2$CH$_2$—); 2,78 (t,2H,CH$_2$CO); 3,69 (t,2H,CH$_2$Cl); 4,5 (s,2H,CH$_2$benzyl); 7,36 (s,5H,aryl).

IR (CDCl$_3$): $\gamma_{max}$ 3.160, 1700, 1555, 1305 cm$^{-1}$

(b) and (c) Preparation of 5-(5-aminovaleroylamino)-2-sulfonamide-1,3,4-thiadiazole (Rende 027)

The preparation of 5-(5-aminovaleroylamino)-2-sulfonamide-1,3,4-thiadiazole is performed starting from 2 g of 5-chlorovaleroylamino-2-benzylmercapto-1,3,4-thiadiazole and it follows the synthesis route already disclosed in example 1 through the formation, with chlorine in acid medium, of the corresponding sulfonyl chloride and subsequent reaction with liquid ammonia. The raw product so obtained is crystallized directly from 95% ethanol so yielding 750 mg of the product with melting point 209°-212° C. and 45% yield.

$^1$H—NMR 80 MHz (DMSO-d$_6$) δ=1,7 (m,4H,—CH$_2$CH$_2$—); 2,5 (t,2H,—CH$_2$CO); 3,6 (t,2H,CH$_2$NH$_2$); 8,3 (s,2H,SO$_2$NH$_2$).

IR (KBr): $\gamma_{max}$ 3360, 3200, 3100, 1690, 1565, 1380, 1175, 910 cm$^{-1}$ Analysis (C$_7$H$_{13}$N$_5$O$_3$S$_2$) Calcd.: C, 30.09; H, 4.69; N, 25.07; S, 22.96; Found: C, 29.74; H, 4.29; N, 22.17; S, 21.90.

EXAMPLE 13

5-Phthalimidobutynoylamino-2-sulfonamido-1,3,4-thiadiazole (Rende 031)

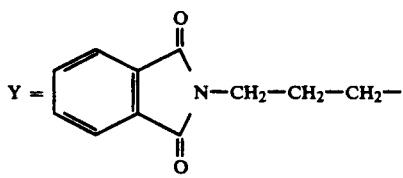

Series I

SCHEME C, route steps (i), (e), (a), (b), (c)

(i) Preparation of gamma-phthalimidobutyric acid 2 g of gamma-aminobutyric acid is reacted with an equimolar amount (2.87 g) of phthalic anhydride by dry melting at 150° C. The reaction product is crystallized from ethanol/water (1/2) so yielding 4 g of gamma-phthalimidobutyric acid with melting point 120°-123° C. and 88% yield.

(1) Preparation of 5-phthalimidobutyroyl chloride 1 g of gamma-phthalimidobutyric acid is reacted with 0.45 ml of thionyl chloride (1/1.5 molar ratio) at 70° C. for 5 hours. The excess thionyl chloride is then removed in vacuo and the residue is purified by crystallization from xylene/petroleum ether 30°-50° C. (1/2 ratio). 950 mg of phthalimidobutyric chloride is obtained with 77% yield.

(a) Preparation of 5-phthalimidobutyroylamino-2-benzylmercapto-1,3,4-thiadiazole 0.8 ml (5.7 mmole) of triethylamine, 950 mg (3.8 mmole) of 5-phthalimidobutyroyl chloride and 100 mg of 4-DMAP are added under nitrogen atmosphere to 845 mg (3.8 mmole) of 5-amino-2-benzylmercapto-1,3,4-thiadiazole suspended in 10 ml of CH$_2$Cl$_2$.

The reaction mixture is neutralized with 0.1N HCl after 3 hours and then it is extracted with CH$_2$Cl$_2$. The organic extracts are then washed with water and dried over sodium sulfate. After removal of the solvent, the raw product is crystallized from ethanol so yielding 660 mg of 5-phthalimidobutyroylamino-2-benzylmercapto-1,3,4-thiadiazole with melting point 128°-131° C. and 40% yield. 420 mg of 5-amino-2-benzylmercapto-1,3,4-thiadiazole (50%) is recovered from crystallization waters.

$^1$H—NMR (80 MHz) (CDCl$_3$): δ=2,25 (m,2H,CH$_2$); 2,7 (t,2H,CH$_2$CO); 4,18 (t,2H,NCH$_2$); 4,5 (s,2H,CH$_2$benzyl); 7,3 (d,5H,aryl); 7,8 (m,4H,phthalimide)

(b) Preparation of 5-phthalimidobutyroylamino-2-sulfonylchloride-1,3,4-thiadiazole A suspension of 600 mg of 5-phthalimidobutyroylamino-2-benzylmercapto-1,3,4-thiadiazole in 12 ml of acetic acid (33% water solution) is kept at 0° C. under chlorine atmosphere for 3 hours. During that period changes are observed in the appearance of the solid; the excess chlorine present in the reaction medium is then removed and the solid is filtered off and washed with cold water. 550 mg of raw sulfonyl chloride is obtained which is employed for the next reaction.

(c) Preparation of 5-phthalimidobutyroylamino-2-sulfonamido-1,4-thiadiazole (Rende 031)

550 mg of sulfonyl chloride is added slowly and under nitrogen atmosphere into 20 ml of freshly condensed liquid ammonia at −78° C. When the addition is complete, ammonia is removed putting the reaction flask into a water bath at room temperature.

The raw sulfonamide so obtained is purified through dissolution of the residue in 2N NH$_4$OH and subsequent acidification to pH 4 by addition of conc. HCl until reaching pH 4.

After filtering and drying the precipitate, 100 mg of the product is obtained with melting point 226°-229° C. and 31% yield starting from the corresponding benzyl compound.

$^1$H—NMR 300 MHz (DMSO-d$_6$): δ=2,2 (q,2H,CH$_2$); 2,7(t,2H,CH$_2$CO); 4,1 (t,2H,NCH$_2$); 7,8 (m,4H,phthalim); 8,4 (s',2H,SO$_2$NH$_2$)

IR (KBr): $\gamma_{max}$ 3250, 2930, 1690, 1360, 1170 cm$^{-1}$

Analysis (C$_{14}$H$_{13}$N$_5$O$_5$S$_2$) Calcd.: C, 42.52; H, 3.31; N, 17.71; S, 16.22; Found: C, 42.75; H, 3.47; N, 18.98; S, 17.51.

EXAMPLE 14

5-Phthalimidobutyroylamino-2-sulfonamido-1,3,4-thiadiazole (Rende 031)

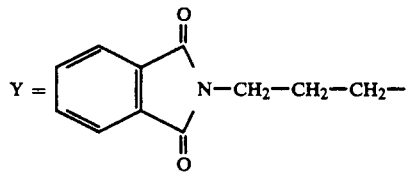

Series I

SCHEME C, route steps (m), (1), (a), (b), (c)

(m) Preparation of gamma-phthalimidobutyric acid 3 g of 4-chlorobutyric acid is reacted with 4.5 g (molar ratio 1/1) of potassium phthalimide in 60 ml of DMF with stirring and at room temperature.

The reaction mixture is then treated after 2 hours by adding water and filtering the precipitate so formed. After crystallization from ethanol, 4.6 g of phthalimidobutyric acid is obtained with 80% yield.

(1), (a), (b) and (c) Preparation of 5-phthalimidobutyroylamino-2-sulfonamido-1,3,4-thiadiazole (Rende 031)

The same steps are followed that correspond to those of the preceding example.

EXAMPLE 15

5-Methylsuccinoylamino-4-methyl-2-sulfonamido-1,3,4-thiadiazole (Rende 024)

Series III, Y=CH$_3$OCO(CH$_2$)$_2$—
SCHEME D, route steps (n), (b'), (c')

(n) Methylation reaction of 5-methylsuccinoylamino-2-benzylmercapto-1,3,4-thiadiazole 600 mg (13 mmole) of a 50% sodium hydride oil suspension is added to 3 g (9 mmole) of 5-methylsuccinoylamino-2)benzylmercapto-1,3,4-thiadiazole (obtained according to the Example 2, steps (d) and (d'), or according to the Example 3, steps (a) and (e)) dissolved into 90 ml of anhydrous THF.

8 ml of CH$_3$I (molar ratio 10/1) is slowly added to the mixture with stirring under nitrogen while checking the reaction through TLC(5% methanol in chloroform).

The reaction mixture is neutralized with 2N HCl after 3 hours and then extracted three times with ether; the organic phase is washed with water and dried. The raw product is made up of a mixture which is purified through silica gel column chromatography eluting with ethyl acetate/petroleum ether 40/60.

1.86 g of 5-methylsuccinoylamino-4-methyl-2-benzyl-mercapto-1,3,4-thiadiazole (A) is obtained from such separation, with melting point 76°-78° C. (60% yield) and 800 mg of 5-methylsuccinoyl-N-methylamino-2-benzylmercapto-1,3,4-thiadiazole (B) (26% yield).

(A) $^1$H—NMR 60 MHz (CDCl$_3$): δ=2,8 (dt,4H,—CH$_2$CH$_2$—); 3,6 (s,3H,OCH$_3$); 3,8 (s,3H,CH$_3$); 4,3 (s,2H,CH$_2$benzyl) 7,2 (s,5H,aryl) IR (CHCl$_3$): γ$_{max}$ 2960, 1740, 1620 cm$^{-1}$ (B) $^1$H—NMR 60 MHz (CDCl$_3$): δ=2,8 (dt,4H,—CH$_2$CH$_2$—); 3,63 (s,3H,OCH$_3$); 3,7 (s,3H,CH$_3$); 4,4 (s,2H,CH$_2$benzyl) 7,25 (s,5H,aryl) IR (CHCl$_3$): γ$_{max}$ 2970, 1735, 1675, 1410 cm$^{-1}$ (b') Preparation of 5-methylsucinoylamino-4-methyl-2-sulfonylchloride-1,3,4-thiadiazole Chlorine is bubbled through a suspension of 1 g of 5-methylsuccinoylamino-4-methyl-2-benzylmercapto-1,3,4-thiadiazole in 15 ml of a 33% acetic acid water solution while the mixture is kept under stirring at 0° C.

The reaction is checked through TLC (40% acetate in petroleum ether) and it is shown to be complete within 2 hours. The chloride so formed is extracted with methylene chloride, the organic phase is washed at 0° C. with a NaHCO$_3$ saturated solution and next with water until it is neutral and finally dried over sodium sulfate. 920 mg of the product is obtained which is immediately employed for the subsequent reaction.

As already discussed in the preceding disclosure, a particular care is to be taken in checking the temperature during preparation, because of the instability of sulfonyl chloride in compounds of the series II and III.

(c') Preparation of 5-methylsuccinoylamino-4-methyl-2-sulfonamido-1,3,4-thiadiazole (Rende 024)

900 mg of 5-methylsuccinoylamino-4-methyl-2-sulfonylchloride-1,3,4-thiadiazole dissolved in 5 ml of anhydrous THF is slowly added under nitrogen to 25 ml of freshly condensed liquid ammonia at −78° C. Ammonia is removed by leaving the reaction vessel at room temperature. The residue is purified by dissolution into 2N NH$_4$OH and filtration of the insoluble residue.

Waters are acidified with conc. HCl up to pH 4 and the precipitate so formed yields 320 mg of 5-methylsuccinoylamino-4-methyl-2-sulfonamido-1,3,4-thiadiazole, melting point 135°-137° C.; yield=38%.

$^1$H—NMR 300 MHz (DMSO-d$_6$): δ=2,62 (t,2H,CH$_2$); 2,81 (t,2H,CH$_2$); 3,6 (s,3H,OCH$_3$); 3,97 (s,3H,CH$_3$); 8,23 (s',2H,SO$_2$NH$_2$)

IR (KBr): γ$_{max}$ 3318, 3220, 3120, 1715, 1642, 1330, 1180 cm$^{-1}$ $^{13}$C—NMR (DMSO-d$_6$): 28,7(C-9), 33,7(C-8) 38,1(NCH$_3$) 51,2(C-11) 157,6(C-5) 164,2(CSO$_2$NH$_2$) 172,7(CO) 180,9(CONH)

Analysis (C$_8$H$_{12}$N$_4$O$_5$S$_2$) Calcd.: C, 31.16; H, 3.92; N, 18.07; S, 20.79; Found: C, 31.70; H, 3.86; N, 18.09; S, 20.55.

EXAMPLE 16

5-Methylsuccinoyl-N-methylamino-2-sulfonamido-1,3,4-thiadiazole (Rende 026)

Series II, Y=CH$_3$OCO(CH$_2$)$_2$— SCHEME D, route steps (n), (b), (c)

(n) Methylation reaction of 5-methylsucinoylamino-2-benzylmercapto-1,3,4-thiadiazole The procedure is the same as that followed in the preceding example.

(b) Preparation of 5-methylsuccinoyl-N-methylamino-2-sulfonylchloride-1,3,4-thiadiazole Chlorine gas is bubbled through a suspension of 800 mg of 5-methylsuccinoyl-N-methylamino-2-benzylmercapto-1,3,4-thiadiazole in 10 ml of a 33% acetic acid water solution, while the mixture is kept stirred at 0° C.

The reaction is stopped after 3 hours and the reaction mixture is treated by methylene chloride extraction. The organic extracts are then washed with a NaHCO$_3$ saturated solution at 0° C. and then with water up to neutrality and finally dried over anhydrous sodium sulfate.

670 mg of an oily compound is obtained which is employed in the raw state for the formation of the corresponding sulfonamide.

(c) Preparation of 5-methylsuccinoyl-N-methylamino-2-sulfonamido-1,3,4-thiadiazole (Rende 026)

670 mg of 5-methylsuccinoyl-N-methylamino-2-sulfonylchloride-1,3,4-thiadiazole, dissolved into 3 ml of anhydrous THF, is slowly added into 25 ml of freshly condensed liquid ammonia at −78° C. under nitrogen.

When the addition has been completed, ammonia is removed by putting the reaction vessel into a water bath at room temperature, and the residue is dissolved into 2N NH$_3$ at pH 8 and next precipitated by addition of conc. HCl up to pH 4.

The precipitate so formed is filtered and dried so that 250 mg of the product is obtained, with melting point 120°-124° C. and 35% yield starting from 5-methylsuccinoyl-N-methylamino-2-benzylmercapto-1,3,4-thiadiazole $^1$H—NMR 80 MHz (DMSO-d$_6$): δ=2,8 (dt,4H,—CH$_2$CH$_2$—); 3,6 (s,3H,OCH$_3$); 3,72 (s,3H,CH$_3$); 8,2 (s',2H,SO$_2$NH$_2$)

IR (KBr): γ$_{max}$ 3300, 3250, 1750, 1660, 1350, 1175 cm$^{-1}$

EXAMPLE 17

5-Pentylsuccinoylamino-4-methyl-2-sulfonamido-1,3,4-thiadiazole (Rende 035)

Series III, Y=CH$_3$(CH$_2$)$_4$OCO(CH$_2$)$_2$— SCHEME D, route steps (n), (b'), (c')

(n) Methylation reaction of 5-pentylsuccinoylamino-2-benzylmercapto-1,3,4-thiadiazole 500 mg (10,5 mmole) of a 50% sodium iodide oil suspension is added to 3 g (7.8 mmole) of 5-pentylsuccinoylamino-2-benzylmercapto-1,3,4-thiadiazole (obtained for example according to the Example 4, steps (d) and (a')), dissolved into 100 ml of anhydrous THF.

10 ml of CH$_3$I is slowly added to the mixture (molar ratio 10/1) with stirring under nitrogen (check performed through TLC, 2% acetone in chloroform).

The reaction is shown to be complete in 3 hours. The reaction mixture is then diluted with 200 ml of acetate and washed first with acidified water and then with water up to neutrality; the organic extracts are then dried and the raw product is purified through silica gel column chromatography.

1.94 g of 5-pentylsuccinoylamino-4-methyl-2-benzylmercapto-1,3,4-thiadiazole (A) is obtained from such separation with 62% yield, as well as 870 mg of 5-pentylsuccinoyl-N-methylamino-2-benzylmercapto-1,3,4-thiadiazole (B) with 27% yield.

(A) $^1$H—NMR 60 MHz (CDCl$_3$): δ=0,85 (t,3H,CH$_3$); 1,4 (m,6H,(CH$_2$)$_3$); 2,8 (m,4H,—CH$_2$CH$_2$—); 3,85 (s,3H,CH$_3$); 4,1 (t,2H,OCH$_2$); 4,3 (s,2H,CH$_2$benzyl); 7,3 (s,5H,aryl) IR (CHCl$_3$): γ$_{max}$ 2925, 1730, 1620, 1380, 975 cm$^{-1}$ (B) $^1$H—NMR 60 MHz (CDCl$_3$): δ=0,9 (t,3H,CH$_3$); 1,4 (m,6H,(CH$_2$)$_3$); 2,85 (m,4H,—CH$_2$—CH$_2$); 3,79 (s,3H,CH$_3$); 4,2 (t,2H,OCH$_2$); 4,5 (s,2H,CH$_2$benzyl); 7,35 (s,5H,aryl) IR (CHCl$_3$): γ$_{max}$ 2925, 1730, 1670, 1310, 1115 cm$^{-1}$ (b') Preparation of 5-pentylsucinoylamino-4-methyl-2-sulfonylchloride-1,3,4-thiadiazole Chlorine is bubbled through a suspension of 1.94 g of 5-methylsuccinoylamino-4-methyl-2-benzylmercapto-1,3,4-thiadiazole in 30 ml of a 33% acetic acid water solution, while the mixture is kept stirred at 0° C.

The disappearance of the starting product is controlled through TLC (5% methanol in chloroform) and it shows complete within 2 hours.

The chloride so formed is extracted by means of CH$_2$Cl$_2$, the organic phase is washed at 0° C. with a saturated solution of NaHCO$_3$, then with water up to neutrality and finally it is dried over anhydrous sodium sulfate.

The cold evaporation of the organic solvent yields 1.7 g of the product which is immediately employed for the next reaction.

(c') Preparation of 5-pentylsuccinoylamino-4-methyl-2-sulfonamido-1,3,4-thiadiazole (Rende 035)

1.7 g of 5-pentylsuccinoylamino-4-methyl-2-sulfonilchloride-1,3,4-thiadiazole dissolved into 6 ml of anhydrous THF is slowly added to 40 ml of freshly condensed liquid ammonia at −78° C. and under nitrogen atmosphere. When the addition has been completed, ammonia is removed by dipping the reaction flask into a water bath. The residue is dissolved with a 2N NH$_4$OH water solution and then acidified to pH 4 with conc. HCl.

An oily product is separated that is extracted twice with ethyl acetate. The organic extracts are then collected together, washed with brine, dried over anhydrous sodium sulfate and the solvent is evaporated off. Purification of the raw sulfonamide is performed by means of silica gel column chromatography, eluting with 5% methanol in chloroform. 1.12 g of the product is obtained with melting point 95°-97° C. and 64% yield starting from the benzyl product.

$^1$H—NMR 300 MHz (DMSO-d$_6$): δ=0,85 (t,3H,CH$_3$); 1,27 (m,4H,—CH$_2$—CH$_2$—); 1,55 (m,2H,CH$_2$); 2,65 (t,2H,CH$_2$CO); 2,82 (t,2H,COCH$_2$); 3,92 (s,3H,CH$_3$); 4,0 (t,2H,OCH$_2$); 8,26 (s,2H,SO$_2$NH$_2$)

$^{13}$C—NMR (DMSO-d$_6$): 13,7(CH$_3$); 21,6(C-14); 27,4(C-12); 27,7(C-13); 29,1(C-9); 33,7(C-8); 38,1(C-4); 63,7(C-11); 157,6(C-5); 164,2(CSO$_2$NH$_2$); 172,2(CO); 181(CON)

IR (CHCl$_3$): γ$_{max}$ 3425, 3345, 2925, 1730, 1625, 1375, 1160 cm$^{-1}$

Analysis (C$_{12}$H$_{20}$N$_4$O$_5$S$_2$) Calcd.: C, 39.55; H, 5.53; N, 15.37; S, 17.59; Found: C, 39.33; H, 5.65; N, 15.16; S, 17.49.

EXAMPLE 18

5-Pentylsuccinoyl-N-methylamino-2-sulfonamido-1,3,4-thiadiazole (Rende 038)

Series II, Y=CH$_3$(CH$_2$)$_4$OCO(CH$_2$)$_2$— SCHEME D, route steps (n), (b), (c)

(n) Methylation reaction of 5-pentylsuccinoylamino-2-benzylmercapto-1,3,4-thiadiazole The procedure is the same as that followed in the preceding example.

(b) Preparation of 5-pentylsuccinoyl-N-methylamino-2-sulfonylchloride-1,3,4-thiadiazole Chlorine is bubbled through a suspension of 800 mg of 5-pentylsuccinoyl-N-methylamino-2-benzylmercapto-1,3,4-thiadiazole in 15 ml of a 33% acetic acid water solution, while the mixture is kept under stirring at 0° C.

The reaction is checked through TLC (2% acetone in chloroform) and is complete in 4 hours.

The chloride so formed is extracted with methylene chloride, the organic phase is washed with a saturated solution of NaHCO$_3$ at 0° C., and subsequently with ice-cold water up to neutrality, and finally it is dried over anhydrous sodium sulfate.

750 mg of the raw product is obtained that is employed for the successive reaction.

(c) Preparation of 5-pentylsuccinoyl-N-methylamino-2-sulfonamide-1,3,4-thiadiazole (Rende 038)

750 mg of sulfonyl chloride dissolved into 3 ml of anhydrous THF is slowly added into 20 ml of freshly condensed liquid ammonia at −78° C. and under nitrogen atmosphere.

Ammonia is removed at room temperature and the residue is dissolved into 2N NH$_4$OH.

The solution acidified with conc. HCl up to pH 4, is extracted twice with ethyl acetate and the organic phase is dried over anhydrous sodium sulfate.

The purification of the sulfonamide is carried out through silica gel column chromatography, eluting with 2% acetone in chloroform.

145 mg of the product is obtained with melting point 83°-87° C. and 20% yield starting from 5-pentylsuccinoyl-N-methylamino-2-benzylmercapto-1,3,4-thiadiazole.

EXAMPLE 19

5-methylsuccinoylamino-2-sulfonamido-1,3,4-thiadiazole (Rende 023)

Series I, Y=CH$_3$OCO(CH$_2$)$_2$— SCHEME E

(o) and (p) Preparation of 5-amino-2-sulfonamido-1,3,4-thiadiazole 17 g of acetazolamide (purchased from Aldrich) is hydrolyzed with 150 ml 10% HCl. The reaction is kept under reflux and stirred, and is monitored by means of TLC (20% methanol in chloroform). After 5 hours the reaction shows to be complete.

The reaction mixture is cooled to room temperature and neutralized with NaOH up to pH 6. After precipitation and filtration under vacuum 12 g of 5-amino-2-sulfonamido-1,3,4-thiadiazole is obtained, with yield of 87%.

(q) Preparation of 5-methylsuccinoylamino-2-sulfonamido-1,3,4-thiadiazole 12 g of 5-amino-2-sulfonamido-1,3,4-thiadiazole is suspended in 60 ml of anhydrous $CH_2Cl_2$; 8.7 ml of $Et_3N$, 170 mg of 5-DMAP and, slowly, 6.5 ml of succinoylchloride monomethyl (3-carbomethoxy-propionylchloride) are then added to such suspension.

The reaction, kept under nitrogen, is followed through TLC (20% methanol in chloroform) and shows to be complete after 5 hours.

In order to obtain the purified product, 40 ml of 25% $NH_4OH$ is added to the reaction mixture and after separation, the aqueous phase is acidified with 37% HCl up to pH 4.

The precipitate so formed is filtered and crystallized from water. 13 g of the final product is obtained, with a yield of 66%.

EXAMPLE 20

5-succinoylamino-2-sulfonamido-1,3,4-thiadiazoic acid (Rende 037)

Series I, $Y=HOCO(CH_2)_2-$ SCHEME E

Preparation of 5-methylsuccinoylamino-2-sulfonamido-1,3,4-thiadiazole (Rende 023)

The preparation is carried out according to example 19.

Preparation of 5-succinoylamino-2-sulfonamido-1,3,4-thiadiazoic acid (Rende 037)

13 g of 5-methylsuccinoylamino-2-sulfonamido-1,3,4-thiadiazole is dissolved in 150 ml of 5% NaOH. The reaction is kept under stirring at 60° C. for 1 hour and 30 min. and is followed by means of TLC (40% methanol in chloroform).

The reaction mixture is then cooled and acidified with 5N HCl up to precipitation of the product. The solid so formed is filtered, washed with water and dried. 8.6 g of the final product is obtained, with a yield of 70%.

This invention has been disclosed, just for illustrative and not for limitative purposes, according to some preferred embodiments of the same, but it is to be understood that modifications and/or changes can be brought in by those who are skilled in the art without departing from its true the spirit and scope.

We claim:

1. Acetazolamide or its N-methyl derivatives, having inhibiting activity of carbonic anhydrase, of the formulae:

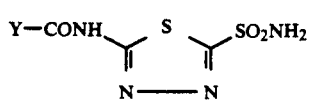
(I)

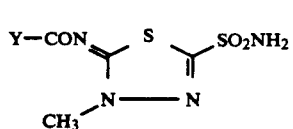
(II)

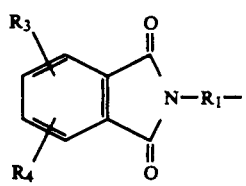
(III)

wherein Y is:

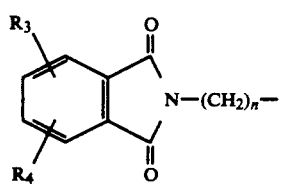

wherein $R_1$ is a straight or branched alkylene or arylalkylene, or a phenylene, $R_2$ is hydrogen or a straight or branched alkyl possibly substituted with halogen, $R_3$ and $R_4$, which can be the same or different from each other, and hydrogen or straight or branched alkyl, and the physiologically acceptable salts thereof.

2. The compounds according to claim 1, wherein Y is the group:

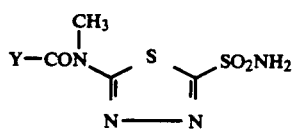

wherein $R_3$ and $R_4$, which can be the same or different from each other, are hydrogen or a lower alkyl of 1–6 carbon atoms and n is an integer between 1 and 10.

3. N-methyl derivatives of acetazolamide, having inhibiting activity of carbonic anhydrase, of the formulae:

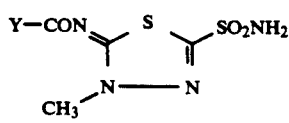

or

wherein Y is one of the following groups:

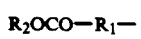

$R_2OCO-R_1-$

-continued

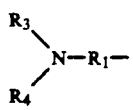

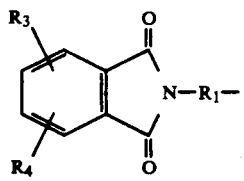

wherein $R_1$ is a straight or branched alkylene or arylalkylene, or a phenylene, $R_2$ is hydrogen or a straight or branched alkyl possibly substituted with halogen, $R_3$ and $R_4$, which can be the same or different from each other, are hydrogen or straight or branched alkyl, and the physiologically acceptable salts thereof.

4. The compounds according to claim 3, wherein Y is the group:

$R_2OCO—(CH_2)_n—$ wherein $R_2$ is hydrogen or a straight or branched alkyl having 1-20 carbon atoms and possibly substituted with halogen, and n is an integer between 1 and 10.

5. The compounds according to claim 3, wherein Y is the group:

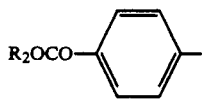

wherein $R_2$ is hydrogen or a straight or branched alkyl having 1-20 carbon atoms.

6. The compounds according to claim 3, wherein Y is the group of the formula:

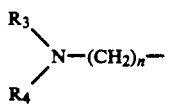

wherein $R_3$ and $R_4$, which can be the same or different from each other, are hydrogen or a lower alkyl of 1-6 carbon atoms, and n is an integer between 1 and 10.

7. The compounds according to claim 3, wherein Y is the group:

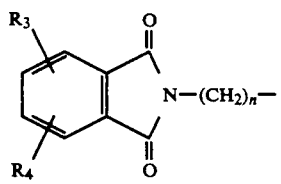

wherein $R_3$ and $R_4$, which can be the same or different from each other, are hydrogen or a lower alkyl of 1-6 carbon atoms and n is an integer between 1 and 10.

* * * * *

UNITED STATES PATENT AND TRADEMARK OFFICE
CERTIFICATE OF CORRECTION

PATENT NO. : 5,010,204

DATED : April 23, 1991

INVENTOR(S) : Simonetta Antonarolli, et al

It is certified that error appears in the above-identified patent and that said Letters Patent is hereby corrected as shown below:

Column 24, line 1, it should read -- EXAMPLE 10 --.

Signed and Sealed this

Sixteenth Day of March, 1993

*Attest:*

STEPHEN G. KUNIN

*Attesting Officer*     Acting Commissioner of Patents and Trademarks